United States Patent [19]

Engel

[11] Patent Number: 4,608,365

[45] Date of Patent: Aug. 26, 1986

[54] TREATMENT OF NEUROLOGIC FUNCTIONS

[75] Inventor: W. King Engel, Los Angeles, Calif.

[73] Assignee: University of Southern California, Los Angeles, Calif.

[21] Appl. No.: 595,214

[22] Filed: Mar. 30, 1984

[51] Int. Cl.$^4$ .............................................. A61K 37/43
[52] U.S. Cl. ...................................................... 514/18
[58] Field of Search .................... 260/112.5 R; 514/18

[56] References Cited

U.S. PATENT DOCUMENTS

| | | | |
|---|---|---|---|
| 3,737,422 | 6/1973 | Flouret | 260/112.5 R |
| 3,746,697 | 7/1973 | Folkers et al. | 260/112.5 R |
| 3,753,969 | 8/1973 | Folkers et al. | 260/112.5 R |
| 3,757,003 | 9/1973 | Folkers | 260/112.5 R |
| 3,816,387 | 6/1974 | Cole et al. | 260/112.5 R |
| 3,833,604 | 9/1974 | Schafer | 260/309 |
| 3,860,570 | 1/1975 | Thomas | 260/112.5 R |
| 3,873,709 | 3/1975 | Plotnikoff | 424/247 |
| 3,912,705 | 10/1975 | Fujino et al. | 260/112.5 R |
| 3,932,623 | 1/1976 | Wilson et al. | 424/177 |
| 3,959,247 | 5/1976 | Fujino et al. | 260/112.5 TR |
| 3,959,248 | 5/1976 | Veber et al. | 260/112.5 R |
| 4,045,556 | 8/1977 | Schwertner et al. | 260/112.5 R |
| 4,066,749 | 1/1978 | Veber et al. | 260/112.5 TR |
| 4,100,152 | 7/1978 | Fujino et al. | 260/112.5 TR |
| 4,125,605 | 11/1978 | Tyson | 424/177 |
| 4,167,563 | 9/1979 | Mikura et al. | 260/112.5 R |
| 4,254,261 | 3/1981 | Miller et al. | 546/203 |
| 4,386,073 | 5/1983 | Kisfaludy et al. | 260/112.5 R |
| 4,426,378 | 1/1984 | Holaday | 424/177 |
| 4,468,382 | 8/1984 | Bacha | 260/112.5 R |

OTHER PUBLICATIONS

Sobue et al., "Thyrotropin-Releasing Hormone and Spinocerebellar Degenerations," *Neurology*, Proceedings of the World Congress of Neurology, Excerpta Medica, 1982, pp. 240–258.

Faden et al., "Thyrotropin-Releasing Hormone Improves Neurologic Recovery After Spinal Trauma in Cats," *The New England Journal of Medicine*, 1981, vol. 305, No. 18, pp. 1063–1067.

Engel, et al., "Effect on Weakness and Spasticity in Amyotrophic Lateral Sclerosis of Thyrotropin-Releasing Hormone," *Lancet*, Jun. 9, 1983, pp. 73–75.

John W. Holaday, et al., "Protirelin (TRH)", *Arch. Intern. Med.*, vol. 144, Jun. 1984, pp. 1138–1140.

*MDA Colloquium*, Muscle & Nerve, Jul./Aug. 1985, p. 463.

Benjamin Rix Brooks, et al., "Extracellular Cyclic Nucleotide Metabolism in the Human Central Nervous System," *Neurobiology of Cerebrospinal Fluid*, Ed. James H. Wood, M.D., Plenum Press, New York, 1980, pp. 113–139.

Richard B. Mailman, et al., "Change in Brain cGMP Content," *Journal of Pharmacology and Experimental Therapeutics*, vol. 208, 1979, pp. 169–175.

Richard B. Mailman, et al., "Thyrotropin-Releasing Hormone Reversal of Ethanol Induced Decreases in Cerebellar cGMP," *Nature*, vol. 272, Apr. 1978, pp. 832–833.

K. Krnjevic, et al., "Is Cyclic Gnuanosine Monophosphate the Internal 'Second Messenger' for Cholinergic Actions on Central Neurons?," *Can. J. Physio. Pharmacol.*, vol. 54, 1976, pp. 172–176.

K. Krnjevic, et al., "Cyclic Nucleotides in Spinal Cells," *Can. J. Physio. Pharmacol.*, vol. 54, 1976, pp. 416–421.

Pages from "Neurochemical Alterations in Parkinson's Disease," Ed. James H. Wood, M.D., *Neurobiology of Cerebrospinal Fluid*, Plenum Press, New York, 1980, pp. 208–210.

W. King Engel, et al., "Phthalazinol, Thrombocytopenia, and Amyotrophic Lateral Sclerosis," *Arch. Neurol.*, vol. 37, May 1980, p. 320.

Jerry R. Mendell, M.D., et al., "Amyotrophic Lateral Sclerosis," *Arch. Neurol.*, vol. 25, Oct. 1971, pp. 320–325. Notes of Dr. Engel regarding cAMP and cGMP studies.

Alan I. Faden, et al., "Comparison of Thyrotropin-Releasing Hormone (TRH), Naloxone, and Dexamethasone Treatments in Experimental Spinal Injury," *Neurology*, vol. 33, Jun. 1983, pp. 673–678.

Alan I. Faden, et al., "Effect of TRH Analogs on Neurologic Recovery After Experimental Spinal Trauma," *Neurology*, vol. 35, Sep. 1985, pp. 1331–1334.

Alan I. Faden, M.D., "Opiate Antagonists and Thyrotropin-Releasing Hormone," *JAMA*, Sep. 21, 1984, vol. 252, No. 11, pp. 1452–1454.

Alan I. Faden, et al., "Thyrotropin-Releasing Hormone in Experimental Spinal Injury: Dose Response and Late Treatment," *Neurology*, vol. 34, Oct. 1984, pp. 1280–1284.

Giora Feuerstein, et al., "Hypotension Produced by Platelet-Activating Factor is Reversed by Throtropin-Releasing Hormone," *Circulatory Shock* 13, 1984, pp. 255–260.

Warren E. Lux, Jr., et al., "Thyrotropin-Releasing Hormone Reverses Experimental Anaphylactic Shock Through Non-Endorphin-Related Mechanisms," *European Journal of Pharmacology*, 90, 1983, pp. 301–302.

*Primary Examiner*—Delbert R. Phillips
*Attorney, Agent, or Firm*—Nilsson, Robbins, Dalgarn, Berliner, Carson & Wurst

[57] ABSTRACT

A treatment is provided for the amelioration of symptoms of amyotrophic lateral sclerosis and other conditions which result from dysfunction of lower or upper motor neurons by the administration of doses of thyrotropin-releasing hormone by intravenous infusion or subcutaneous injection.

36 Claims, No Drawings

TREATMENT OF NEUROLOGIC FUNCTIONS

FIELD OF THE INVENTION

The invention hereinafter set forth relates to the fields of medicine and biochemistry, and more specifically to the treatment of neurologic disorders.

BACKGROUND AND SUMMARY OF THE INVENTION

The nervous system has functions that can be broadly categorized as motor, sensory and cognitive functions, and further subcategories can be determined within these groups. For example, normal motor functions relate to voluntary movements and reflex movements, and the anatomic substratum of voluntary movements involves two classes of neurons. The upper motor neurons carry impulses (messages) from the brain to the lower motor neurons located at all levels of the brainstem and spinal cord. The lower motor neurons, in turn, as the "final common path" extend long axonal processes that command movement by voluntary muscles throughout the body. The voluntary movements are controlled by a finely-tuned system executing willed movements of the person, which can be perturbed in a number of ways.

Disorders of upper motor neurons and lower motor neurons affect not only voluntary movements, but also other circuits to allow excessive, undesired involuntary movements resulting in several types of involuntary movement disorders. Disorders of the upper motor neurons or lower motor neurons may be caused by:

(a) systemic damage preferentially involving certain neuronal systems (e.g., caused by metabolic, toxic, hereditary or other unknown mechanisms); or (b) non-systemic, non-preferential damage (e.g., caused by stroke, multiple sclerosis, meningitis, abscess, cerebral palsy, or injury of the brain or spinal cord at birth or later).

Whatever the actual cause of neurologic damage, abnormality of upper motor neuron function results in spasticity (causing slowness, stiffness and weakness of movement), commonly accompanied by clonus (repetitive involuntary movements) and muscle spasms. Abnormality of lower motor neuron function results in weakness, commonly associated with painful muscle cramps.

Treatment of clinical problems caused by upper motor neuron or lower motor neuron abnormality can be either disease-specific or non-specific. Effectiveness of a disease-specific treatment is confined to that disease (e.g., vitamin $B_{12}$ in $B_{12}$ deficiency), whereas non-specific treatment, termed "symptomatic treatment", benefits the symptoms regardless of causes (e.g., aspirin for headache and other pain, and antihypertensive drugs for various kinds of hypertension). Symptomatic treatment of upper motor neuron- or lower motor neuron-caused clinical abnormalities can improve motor (movement) functions in a wide variety of activities of daily living, such as walking, talking, swallowing, breathing and other arm, leg, neck and finger movements. Many of these abnormalities and symptoms in various diseases have not been alleviated or treated despite the advances in medicine in recent years.

For example, amyotrophic lateral sclerosis is a progressive terminal disease with both upper and lower motor neuron involvement. Adult-onset primary lateral sclerosis, adrenomyeloneuropathy and multiple sclerosis each involve upper motor neuron dysfunction. Lower motor neuron abnormalities are typical of juvenile proximal spinal muscular atrophy, chronic adult progressive muscular atrophy and chronic hereditary dysneuronal neuropathy (one form of Charcot-Marie-Tooth disease). Thus, it should be apparent that any therapeutic agent which would alleviate the motor neuron-related symptoms of such diseases would have broad applicability in the treatment of a wide variety of neurologic functions.

It is evident that in the above-described disorders, one set of motor symptoms may result from neuronal deterioration such as structural or functional abnormalities of the lower motor neurons (i.e., ventral horn or anterior horn neurons) or the lower motor neuron system (i.e., neuronal pathways influencing the lower motor neurons. In addition, another set of motor symptoms may result from abnormalities of the upper motor neurons, e.g., the corticospinal tracts and perhaps other suprasegmental pathways impinging on the lower motor neurons as the final common path.

While I do not wish to be bound to any particular theory, it appears that various neurologic disorders causing spasticity and/or weakness (for example, in both the hereditary and sporadic forms of amyotrophic lateral sclerosis) are associated with remediable biochemical defects.

According to the present invention, a replaceable transmitter-like and/or trophic-like moiety is provided for the improvement of neurologic function. Thyrotropin-releasing hormone is seen to comprise an active moiety that has been shown to produce marked improvement in neurologic and neuromuscular functions, particularly those caused by a deficiency in the function of either lower or upper neurons.

As described in the examples hereinafter set forth, thyrotropin-releasing hormone causes improvement of symptoms of malfunction of both lower and upper motor neurons. This improvement occurs in conditions involving lower motor neuron underactivity (e.g., muscle weakness) and overactivity (e.g., muscle cramps) as well as conditions related to defective activity of the upper motor neurons, for example, muscle spasticity, clonus, spasms, withdrawal reflexes and weakness.

Thyrotropin-releasing hormone (TRH), L-pyroglutamyl-L-histidyl-L-prolinamide) is a tripeptide with blocked N- and C-terminal residues, and is considered common to mammalian species including man. TRH has been isolated and identified from ovine and porcine hypothalami, and more recently has been synthesized de novo in the laboratory. It has been shown to have the following structure:

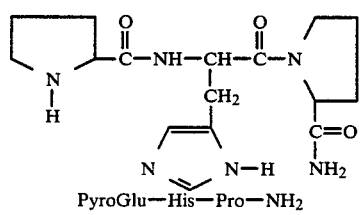

PyroGlu—His—Pro—NH$_2$

Various aspects of the endocrinology of this hormone have been suggested, including the ability of hypothalamically-originating TRH to release not only thyroid-stimulating hormone but also prolactin from, respectively, thyrotrope and mammitrope cells in the anterior pituitary. In addition, it has been demonstrated that the distribution of TRH is not limited to the hypothalamus, but that more than seventy percent of the total TRH found in the central nervous system (brain and spinal cord) is extra-hypothalamic. Further studies have shown that TRH is also found in the gastro-intestinal tract, placenta, retina and other locations. In general, TRH has been suggested to play a neurotransmitter or neuromodulator role in the normal central nervous system, but has not been shown to be of any direct therapeutic benefit in the continuous treatment of neurologic disorders or pain.

Presently, TRH has been used only in certain tests to determine pituitary function in a single intravenous dosage of 300–500 μg, and for this purpose is marketed as an aqueous solution containing 0.5 mg/ml TRH and 9.0 mg/ml sodium chloride adjusted to a neutral pH with hydrogen chloride.

DETAILED DESCRIPTION

As required, a detailed illustrative embodiment of the invention is disclosed herein. However, it is to be understood that this embodiment merely exemplifies the invention which may take forms that are different from the illustration disclosed. Therefore, specific details are not to be interpreted as necessarily limiting, but rather as forming a basis for the claims which define the scope of the invention.

In brief summary, doses of thyrotropin-releasing hormone provide a substantial increase in neuromuscular function and strength. For example, when given to patients with amyotrophic lateral sclerosis (ALS), TRH produced a marked improvement of functions caused by deficiency in the function of lower motor neurons (weakness) and upper motor neurons (spasticity). ALS is a relentlessly progressive disease with lower motor neuron and upper motor neuron involvement, usually causing death within one to five years. If the symptoms associated with neurologic diseases such as ALS are caused by motor neurons that are functioning inadequately but are viable, an effective drug with a transmitter-like and/or a trophic (nutritive)-like effect would be expected to produce rapid clinical improvement. Normally, TRH is present in nerve endings (of supraseg-mental origin) in the ventral horn around all bodies of lower motor neutrons and in nerve endings in the region of motor neuron cell bodies in nuclei V, VII and XII as well as of the frontal/motor cortex. While TRH has been shown to influence both lower and upper motor neuron functions in normal laboratory animals, its use in the continuous treatment of human motor neurologic disorders and pain has been heretofore unknown.

EXAMPLE I

Five ALS patients (men aged 36, 60 and 69, women aged 55 and 60, duration of disease one, one, three and one-half, four and three years, respectively) were given TRH as a continuous intravenous infusion. The dose was increased in stages to a continuous infusion of up to 200 mg over a period of twenty-four hours, and the maximum rate was maintained for fourteen to sixteen days. For about one-fifth of the days, the patients were given saline placebo. No definite clinical benefit was noted. Some patients had mild transient nausea, anorexia, and urinary frequency. In two, there were slight transient rises in serum aspartate and alanine aminotransferases. However, it should be noted that this transient rise has not been found in more than fifty subsequent patients treated with TRH in larger, interrupted doses.

EXAMPLE II

Three fasting ALS patients (men aged 37 and 60 and a woman aged 55; duration of disease three-quarters of a year, one and three years, respectively) were each given an intravenous infusion of TRH in which the dose increased in seven steps from 0.5 to 19 mg/minute over sixty to eighty minutes (total dose 320, 432 and 500 mg). The two men had major spasticity from upper motor neuron involvement and weakness from lower motor neuron involvement. At a dose of 2–4 mg/minute movement and strength of the legs, arms, and tongue began to improve, there was decreased spasticity, and the voice became clearer; at 8 mg/minute shivering, tachypnoea (rapid breathing) and sweating began and the patients showed a moderate increase in blood pressure (10–30 points systolic). Shivering, tachypnoea and sweating increased further with rising dosage, and in the two men the infusion was stopped at 19 mg/minute, after 320 and 432 mg total, because of tachypnoea (40–45 breaths per minute) and vigorous shivering. There also was a transient increase in pulse rate (10–15 beats per minute). The men experienced sensations of coolness or warmth of the anterior lower chest and abdomen. One of the men felt "bad all over" at 19 mg/minute. The benefits and side effects of TRH were no longer obvious thirty minutes after the infusion ended, with the less-refined methods of examination used at that time. At that time, a spinal lumbar puncture was performed to obtain cerebrospinal fluid for analysis as hereinafter described. The female patient had no spasticity, only weakness from lower motor neuron involvement. With the TRH infusion, she had only slight subjective improvement in strength without obvious objective improvement or any side-effects of shivering or tachypnoea. Her infusion was stopped when the drug supply was depleted (at 500 mg total dose). The dosage was not stopped because of side-effects of TRH. She transiently experienced a full feeling in the bladder, urge to urinate, a sensation of vaginal pressure, slight sensations of abdominal cramp and nausea and a small increase in blood pressure. A few months later, when this patient was given TRH and evaluated in more detail, she showed slight but definite improvement of muscle strength, as detailed in Example VI. Experience with the additional patients confirmed the observation that there is more shivering side-effect in the patients with more spasticity.

EXAMPLE III

Nine fasting ALS patients (seven men aged 27, 34, 44, 50, 52, 56 and 62, and two women aged 45 and 70; duration of disease, two, three, five-sixths of a year, five-sixths of a year, two and a half, four, one, one and four years, respectively) were given intravenous TRH at rates of 0.5–8 mg/minute, total 500 mg during two to five hours in one day, for one or two days. Due to the fact that the effects during the second day resembled those on the first day in the first two patients (men) and because supplies of TRH were limited, six patients were treated for one day only. Before and throughout TRH administration, motor functions were repeatedly examined, the tests being selected according to the specific clinical involvement in each patient. Testing in all patients was videotaped. At 2–8 mg/minute each man showed striking improvement of muscle weakness and spasticity in some areas of involvement, while in other areas of the same patient there was only moderate or no improvement. For example, muscles (such as biceps, triceps, deltoid, iliopsoas, or peroneal) that could be overcome easily by one finger before TRH administration became completely resistant to the full force of the examiner's hand (i.e., became normal or virtually normal). In one man, thumb abduction and finger-thumb pincer movement, easily overcome before the infusion of TRH, became normal. Vital capacity increased, by as much as one liter. Speech clarity and volume improved. Spasticity of the legs lessened, as evidenced by easier, more rapid and "looser" bicycling-like movement, heel-shin movement and heel-knee tapping of the legs, as well as more agile walking. Ankle clonus decreased or disappeared, including clonus provoked by walking and by the examiner. Extensor plantar (Babinski) responses improved, becoming neutral or normal flexor. Brisk tendon reflexes diminished not at all or only slightly, apparently not as much as did concurrent clonus or extensor plantar responses. Fasciculations appeared to be unchanged. All of the improvements were sustained, with some fluctuation, throughout the infusion and for one-half to one hour afterwards. There was usually some slight improvement still evident twenty hours after the end of the infusion, but no definite improvement thereafter.

The two women had much less benefit and many fewer side-effects than the men. Qualitatively, responses were the same, but quantitatively, their responses resembled those of men on one-half to one-fourth of the TRH dosage.

Side-effects consisted of dose-related sweating, shivering and an increase in rectal temperature of 0.1°–0.9° C. Blood pressure in some patients transiently increased by 5–15% (perhaps related to the blood-pressure rise is the fact that at the time the patients were also undergoing vigorous repeated strength testing). There were inconsistent, slight, brief sensations of warmth or cold in the abdomen, chest, back or limbs, of bladder or rectal fullness, and of vaginal warmth. Some patients yawned occasionally without feeling sleepy. One patient, after drinking liquid, had nausea and vomited, but he insisted that the infusion be continued for the next few hours. It was, and no further incident occurred. Respiratory rate was unchanged in four patients and increased to thirty-six per minute, with sighing, in one man. There was no consistent change of pulse.

EXAMPLE IV

One non-ALS woman, aged 21, with chronic juvenile proximal spinal muscular atrophy from age fourteen months, had slight to moderate improvement of strength in several muscle functions on 1–8 mg/minute intravenous TRH (500 mg total), and experienced no side-effects. She seemed to be about one-fourth to one-eighth as sensitive to TRH as the men.

EXAMPLE V

As an extension of the Example III and IV studies, a total of twenty-three patients (including those of Examples II and IV) were given 156 intravenous dose-days total. The doses and responses were similar to those of Examples III and IV and of Example VI.

EXAMPLE VI

As shown in Examples I–V, intravenous infusion of thyrotropin-releasing hormone improves weakness and spasticity from lower motor neuron and upper motor neuron involvement in patients with amyotrophic lateral sclerosis and proximal spinal muscular atrophy. In an additional study, forty-one ALS patients were treated with 461 days of subcutaneous TRH administered 75–150 mg once daily or 75 mg twice daily. The subcutaneous doses were sometimes administered by patients or spouses. Included were all forms of ALS, and all patients were videotaped pre- and post-treatment. All TRH-treated patients had beneficial responses, including one retreated non-responder from Example II. Saline injections produced no responses. The previously-noted lesser benefit and side-effects in females was less evident.

Benefit and side-effects of TRH administered subcutaneously were qualitatively and quantitatively similar to those of intravenous TRH described in Examples III and IV. At maximum acute effect, results from 75–150 mg administered subcutaneously were similar to those of an intravenous pulse of 25 mg/6 minutes, as judged in ten patients treated both ways. Response times were somewhat different. After subcutaneous injection, increased strength began at one to one-and-a-half minutes (cf. one-half minute after intravenous TRH) and became maximal at one-and-a-half to two minutes. Spasticity, clonus and muscle cramps sometimes increased during the transient shivering (a minor side-effect beginning at three to ten minutes and lasting until thirty to sixty minutes). When shivering diminished, or one to three hours thereafter, all three effects were improved from their before-treatment status or completely abolished or absent. The subjective and objective benefits in strength, cramps, spasticity and clonus often endured undiminished for twenty-four hours and frequently were present to some degree for three days. Some objective improvement of neuromuscular function was evident in some patients as long as ten to twelve days.

The degree of temporary involvement was often quite remarkable. Some patients regained abilities that had been lost for six to twelve months. Examples of functions re-acquired were related to: (a) lower motor neuron hypofunction (weakness), e.g., the ability to lift a full glass of water to the mouth, feed oneself, and raise 30 cm above the head a hand that had not been able to be raised to waist level was substantially improved; arms were perceived as not being heavy; many patients could easily climb eleven flights of stairs (compared to two with difficulty before TRH); fingers were more dexterous; and the ability to get in and out of a car, to turn a doorknob, button a shirt, zip trousers, turn a key in a lock, open a soft drink can and press a deodorant spray was remarkably improved; or (b) upper motor neuron hypofunction (spasticity), e.g., improvements were noted in the ability to walk and pivot unassisted with ease, steadiness and confidence; to walk much farther and without dragging or sliding feet; to walk up or down steps, run, get in and out of bed or a chair or get up from commode by oneself, turn over in bed, bathe oneself, and generally to be more "flexible" in the trunk and neck; to stand with the back and head more erect, articulate understandably, speak louder, whistle and sing. It should be noted that some of these group "b" functions may also have had improvement in a component of clinical abnormality attributable to lower motor neuron abnormality. Swallowing increased, eliminating choking on food and saliva accumulation in the mouth. Neuromuscular stamina clearly increased, and fatigue decreased. Painful "spontaneous" flexor withdrawal reflexes remained eliminated for at least twelve days in some instances. Painful muscle cramps (lower motor neuron abnormality) and spasms, spontaneous clonus and stiffness (all reflecting upper motor neuron abnormality), common in ALS patients and sometimes impairing sleep, were eliminated or lessened for several days in all patients having them. Aching of shoulder (e.g., "frozen shoulder") and hip joints (i.e., joint pains), common in severe ALS, also were temporarily reduced or abolished for at least one to three days.

In this and Example V, the previously noted lesser benefit and side effects in females was less evident. Shivering seemed more prominent in patients with upper motor neuron involvement. New side effects included: very transient taste noted within a few minutes; asthmatic phenomena lasting about five minutes during maximal shivering in two patients with a history of asthma; lessened joint pain, e.g., from a "frozen" shoulder, for about a day in a few patients; and a mild feeling of well-being for a few hours in several patients, perhaps attributable to their pleasure in being stronger.

One woman with multiple sclerosis had shivering-like movements that were greater on the side of her body, especially the leg, with more upper motor neuron involvement. This observation gives rise to the potential use of TRH (or analog, derivative or analog of derivative) to bring out, for diagnostic purposes any subclinical assymetric upper motor neuron involvement that might exist in a patient.

One patient with hereditary ALS had improvement in strength and also improvement in a co-existing head tremor, an involuntary movement. This observation gives rise to the possible benefit of TRH in other types of involuntary movements.

In this and Example V, safety without side-effects and possible benefit on strength of intravenous and subcutaneous TRH was demonstrated, beginning at age fourteen months, in an infant with infantile spinal muscular atrophy using doses on a body-weight basis comparable to adult doses.

In additional tests, patients have been able to self-administer the subcutaneous TRH or it has been administered by the spouse or a friend, thus allowing maintenance of the described palliative effects outside of the clinical environment. In terms of their clinical improvement, some patients prefer subcutaneous injections once-a-day while others prefer multiple daily injections. It should be understood that known methods for providing a timed release of a substance, and, in particular, of TRH (or an analog, derivative, or analog of a derivative) such as those employed for the release of insulin and other drugs, are within the ambit of the invention, as is the possibly eventual oral administration of TRH or the therapeutically-effective analog or moiety thereof.

Also demonstrated in this Example and Example V were lack of significant clinical, biochemical or hematologic side-effects with the TRH at 150–200 mg intravenous or subcutaneous doses, even in patients treated one to three times a week for as long as eight months.

EXAMPLE VII

The intravenous and subcutaneous administration of TRH as described above has also markedly benefited seven non-ALS patients with: (a) weakness from lower motor neuron abnormality (juvenile proximal spinal muscular atrophy) one patient; chronic adult progressive muscular atrophy, two patients; chronic hereditary dysneuronal neuropathy (i.e., one kind of Charcot-Marie-Tooth disorder) one patient; and (b) spasticity and weakness from upper motor neuron abnormality (adult-onset "primary" lateral sclerosis, two patients; adrenomyeloneuropathy, one patient; multiple sclerosis, one patient). The dosage, benefits and side-effects were essentially similar to those described in Examples II, V and VI.

EXAMPLE VIII

It should be noted that in the above-described examples, doses of TRH have had a substantial ameliorative effect on chronic pain. In untreated amyotrophic lateral sclerosis patients, especially in more advanced stages of the disease, aching of joints is common, (e.g., in a "frozen shoulder" or painful hip). Often, the pain is so severe as to impair sleep. After TRH treatment, a striking improvement in such arthritic pain has been noted for as long as one to four days. The reduction of pain was clearly appreciated when the patients were awake, and it also allowed much more restful nights without their being awakened frequently by pain. The pain reduction did not seem to be related to the "unfreezing" (increased movement) at affected joints due to the fact that there was no significant increase in the movement in such joints of the severely-affected patients whose pain lessened. A logical extension of this observation is that pain of many causes, including other forms of arthritic pain, might be lessened by TRH, or an analog, active derivative or analog of an active derivative of TRH.

This analgesic action of TRH, or perhaps a metabolic product thereof, appears to result from direct action in the pain pathway between the end-organ and the cerebral cortex.

SUMMARY OF TREATMENT STUDIES

It should be noted that the TRH administered in Example I was infused at a rate of up to 200 mg. over a twenty-four hour period. In terms of presence in the body at any one time, this amounted to an infusion rate of about 0.14 mg/minute (2 g/minute/kg body weight based upon the average patient weight of 70 kg). Accordingly, and in view of the significant results shown in Examples II–VIII, it appears that an elevated initial dose and consequently a blood level peak, providing a pulse-effect, is required each time TRH is given. Specifically, in Example IV, intravenous infusion at one milligram per minute (over seven times the infusion rate in Example I) produced an improvement of strength in several muscle functions. In Examples II and III, striking improvement was shown at 2 mg/minute intravenously. In Example IV, an acute increase in strength occurred at 4.7 mg/minute intravenously. In Example VI, similarly striking improvement was shown with subcutaneous TRH 150 mg once daily or 75 mg twice daily.

It was found that the administration of therapeutic amounts of TRH can cause moderate to excellent improvement in neurologic deficits of ALS and other patients that are produced by hypofunction of lower motor neurons (weakness in areas of hypotonic, fasciculating atrophic muscles), and by hypofunction of upper motor neurons (spastic slowness of movement, clonus, and extensor plantar responses). Benefit was evident within thirty seconds of the start of intravenous infusion and within ninety seconds of subcutaneous administration. Full-benefit lasted for up to one hour after intravenous infusions. After subcutaneous administration, the beneficial effect in some neurologic functions was objectively sustained up to three days after administration, and subjectively sustained for as long as twelve days in some patients.

Various "side effects" suggested direct or indirect TRH action on neuronal circuits concerned with temperature regulation (shivering, slight hyperthermia, sweating), respiration (tachypnoea) and autonomic sensation or function (bladder, urethral and vaginal sensation). The TRH administered to the patients as described produced no noticeable effect on mood, alertness, excitation, appetite or sleep. In addition, all patients experiencing the various described side-effects considered those side-effects to be minor and desired further TRH treatments. Moreover, such side-effects may be ameliorated in specific instances, for example, phenylpropanolamine has been demonstrated to diminish the shivering side-effect, and dimenhydrate similarly diminishes the rare, occurring nausea side-effect of TRH.

The therapeutic amount of TRH required in any given instance must be empirically determined, as is the case with the type, dosage and frequency of the various therapeutic agents employed in the treatment of diabetes mellitus. From the Examples set forth herein, the proper dosage for an individual patient may be ascertained without undue experimentation.

Specifically, it has been shown that intravenous infusion in excess of 0.14 mg/minute appears to be required in most adult patients, e.g., at least 1.0 mg/minute was shown to be necessary in the patients tested. Based upon an average patient weight of 70 kilograms, infusion at a rate of 14.3 μg/minute/kg of body weight would appear to be a minimum. However, as it appears from subcutaneous studies that an initial dose provides lasting benefits after the blood level of TRH has subsided, it is likely that intravenous infusion could similarly be effective by virtue of an initial peak blood level from each dose, which is subsequently reduced.

In the clinical testing of various patients after subcutaneous administration of TRH, it appears that a dose of at least 50 mg (0.71 mg/kg of body weight) in the form of a single injection once, or a similar amount twice-a-day, is required.

In fact, since the TRH has been shown to be fast-acting, it may be best to have patients self-administer the drug on an "as needed" basis. In fact, this program has been begun with a few patients with beneficial effects.

There were several control aspects of the TRH studies. Prior to intravenous infusion of TRH, the patients were given physiological saline or dextrose-water as a piggyback infusion and did not know when TRH was reaching them or when the dose was increased. The patients given subcutaneous TRH had treatments interspersed with saline placebo injections. Despite careful testing for evidence of possible benefit, low doses of intravenous TRH were not found to be effective at 0.14 mg/minute for two weeks (Example I), nor were doses at 0.5 mg/minute for twenty minutes in Examples II and III. The time course of response was not known before the study and, in fact, it was expected that the onset would be later and the duration of response longer than was actually found. Different patients responded to different doses of TRH, and the sex difference in response (woman apparently less responsive) was not expected. In a given patient not all muscle movements responded; some of those expected to respond did not, i.e., those with the same degree of pre-treatment weakness as movements that showed excellent response. There were three observers, one unaware of the infusion status. In addition, clinical examinations of all patients of Examples III–VII were videotaped and later reviewed by several observers.

In each of the foregoing Examples, the TRH was administered in a normal saline solution containing 100 mg/ml of TRH. The pH of the solution was not adjusted. This particular carrier and strength was selected for its ready availability, the convenience in calculating dosages administered and its similarity to the placebo solution, and additional carriers may be employed as desired. Timed-release carriers would be particularly advantageous, and are within the scope of the invention.

Physiologic Effects of TRH

A. Transient Autorefractory Effect

The continuous intravenous administration of TRH at a rate of 1–8 mg/minute caused, in all patients, waning-waxing of TRH-increased lower motor neuron strength as early as three to thirty minutes. To analyze this phenomenon, four ALS patients were given six-minute intravenous pulses of 4.17 mg/minute of TRH at ten to twenty minute intervals. Each of the first one to five "priming doses" produced or, sustained dramatically-increased strength in responsive muscles. Subsequent identical pulses precipitated an equally dramatic interruption within 18–30 seconds causing rapid loss of all improvement, back to baseline strength or below, i.e., "autorefractoriness." Some weakness of clinically normal limb muscles also sometimes occurred. Eleven autorefractory states of the four patients lasted 12–100 minutes (median 68 minutes) after initial administration of TRH, until spontaneous recovery re-achieved maximal strength benefit. During recovery, strength fluctuated.

Another ALS patient was given 1 mg/minute continuous intravenous TRH, which markedly increased his strength. When the autorefractory state first developed, with loss of strength to baseline, increasing the infusion to 1.5 mg/minute rapidly overcame the "block" within one minute, associated with increased strength. Within another minute, complete autorefractoriness reappeared. Raising the rate to 2 mg/minute again reversed this blockage, with strength increased to maximum in thirty seconds, but autorefractoriness reappeared in 1.5 minutes. Finally, raising the rate to 2.5 mg/minute for nine minutes failed to increase strength. The TRH was stopped, and the autorefractoriness partially reversed at ten minutes. Strength fluctuated between complete blockage and partial reversal for the next 71 minutes until the autorefractoriness fully reversed itself at 81 minutes.

In twenty ALS patients, it was found that 125–150 mg subcutaneous TRH the first day increased strength within one to two minutes. A partial autorefractory state (partial blockage) began by four to ten minutes and lasted, with fluctuations, two to three hours, at which time maximal drug-induced increase of strength became sustained. At twenty-four hours, when TRH-improved strength remained high, another 125–150 mg subcutaneous dose caused marked weakness within two minutes. Recovery from that complete autorefractory effect encompassed widely fluctuating strength every few minutes until maximal drug-induced increase of strength was sustained by two to three hours, and it again endured at least twenty-four hours. During mild-moderate autorefractoriness (blockage), strength transiently increased with the third to sixth repeated contraction, i.e., "facilitation" occurred. Neuromuscular junction testing at 2 and 20 Hz showed no alteration during the autorefractory state. Possible mechanisms for autorefractoriness, presumably involving the lower motor neuron soma/dendrites and/or neurons afferent thereto, include: TRH desensitization or block of the TRH-receptor; plasmalemmal effects of TRH derivatives histidine-proline diketopiperazine (or their derivatives), pyroglutamate (which can become glutamate and then GABA or glycine), deamino-TRH, histidine and proline; and intracellular effects via various messengers. In normal animals, repeated micropipetting of TRH near lower motor neurons has been shown by others to cause a similar prolonged unresponsiveness. The mechanism of autorefractoriness may be, in general, related to the excellent clinical anti-spasticity benefits of TRH, and non-excitatory TRH analogs may be employed within the spirit of the invention to enhance this type of clinical improvement. In patients repeatedly treated with TRH either intravenously or subcutaneously, as long as eight months, there was no diminution of beneficial response attributable to drug resistance. The transient autorefractory state described above does not interfere with long-term benefit.

Thus, it appears that the autorefractory effect results from a temporary excess of TRH. This should be borne in mind when the dose and dosage of the TRH is determined. In particular, autorefractory effects after an injection indicate that a decrease in amount per dose may be desirable, and/or that subsequent doses may be spread further apart.

B. Pharmacokinetics in Patient Cerebrospinal Fluid

In an initial study, TRH was undetectable in cerebrospinal fluid (CSF) of seven of eight ALS patients (<20 pg/ml) and was 24 pg/ml in one patient (literature control values 44.2±6.8 [mean±SE] pg/ml for males and 38.1±6.5 for females). TRH was also undetectable in a patient with non-ALS spasticity. Subsequently, analysis of a total of 36 ALS patients and 71 disease-controls also showed lower values in ALS patients and non-ALS spasticity patients, but the differences were less pronounced and indicated that low CSF TRH is not disease-specific to ALS. While four of the ALS patients who received intravenous TRH 200 mg/24 hours for two weeks achieved cerebrospinal fluid TRH levels of 46, 163, 197 and 453 pg/ml without clinical benefit, two male ALS patients receiving intravenous TRH infusion of 19 mg/minute for ten minutes at the end of a one hour increasing dosage achieved cerebrospinal fluid TRH levels as high as 977 and 2095 pg/ml concurrent with clinical improvement. TRH assays of five Example III patients have also shown major increments, to as high as 5368 pg/ml (normal less than about 100).

Further studies of patient CSF showed that baseline histidine-proline diketopiperazine (cyclo-HisPro), an initial product (derivative) of the metabolic breakdown of TRH that itself is pharmacologically active in animals, was not altered in ten ALS patients compared with twenty-five disease-controls. With TRH intravenous infusions, levels of cyclo-HisPro as high as 10,508 pg/ml were achieved (normal less than about 600), demonstrating that large amounts of this derivative can enter the CSF.

In three ALS patients given 25 mg TRH intravenously during 6 minutes, concommitant TRH values were measured in the plasma and serum at 0, 6 and 12 minutes. While the plasma levels rose abruptly, the CSF rose only slightly or not at all, demonstrating that clinical benefit, which was evident in all three patients within one-half to two minutes into the infusion, is not necessarily accompanied by very high levels of TRH in CSF. However, lumbar CSF levels are not good, rapid indicators of spinal cord tissue levels of a substance.

C. Possible Mechanisms of the Clinical Benefit

The herein-described Examples demonstrate that exogenous TRH produces a transmitter-like, and possibly a trophic-like, influence and thereby improves function of affected and/or normal lower motor neurons to increase muscle strength, as well as reduces abnormally excessive lower motor neuron activity (e.g., that resulting in spasticity, spasms and cramps). Endogenous, like exogenous, TRH might normally have these dual activating and suppressing actions by acting on TRH (or other) receptors of the lower motor neurons, on TRH (or other) receptors of upper motor neurons, and perhaps on TRH (or other) receptors of other neurons ending on lower or upper motor neurons. The active molecule in these systems could be TRH or a derivative, such as histidine-proline-diketopiperazine (the chemistry of which was described by Prasad, et al. in *Peptides* 1982, 3: 591–598; Peterkofsky et al. in *Neuropeptides* 1980, 1: 105–118 and Mori, et al. in *Brain Res.* 1982, 231: 451–453; the teachings of which are incorporated herein by reference) or deamino-TRH, the chemistry of which was described by Boschi et al. in *Neurosci Lett.* 1980; 16: 209–12 and Griffiths et al. in *Lancet* 1981, i: 834–5, which are similarly incorporated herein by reference) single amino acids (pyroglutamate, histidine, proline) or their products (e.g., glutamate, GABA, glycine). Whether there is any pathogenic deficit of endogenous TRH related to the motor systems in ALS or the other disorders TRH benefits is unknown.

The excitatory effect on the lower motor neurons following the administration of TRH does not appear to be a phenomenon of the neuromuscular junction because standard neuromuscular junction testing at 2 and 20 Hz showed no alteration during that excitation. Therefore, the site of TRH action in the patients appears to be at the lower motor neuron soma/dendrites in the spinal cord and/or neurons afferent to the lower motor neurons, as set forth above.

The rapid effect of TRH on lower motor neurons appearing within one-half minute after intravenous administration and one and one-half to two minutes after subcutaneous administration to increase muscle strength, appears to be, in a general sense, an "excitatory," "transmitter-like" action. "Transmitter-like," as used herein, includes not only direct excitatory (or facilitatory) and inhibitory actions on the lower motor neurons, but also any action on lower motor neurons or afferents thereto that results indirectly in such an effect. That excitatory TRH action, increasing patients' strength, is either directly excitatory or facilitatory and perhaps analogous to the lower motor neuron facilitation of glutamate excitation noted with TRH micropipetted into spinal cords of normal amphibia (Nicoll, *J. Pharmac. Exp. Therap.* 1978; 207: 817–24; Phillis et al., *Can. J. Physiol. Pharmacol.* 1979; 57: 887–99 and rodents, White *Abstr. Soc. Neurosci* 1983, 9: 714, and in other animal studies. An inhibitory transmitter-like action seems likely to underlie both the rapid-onset autorefractory phenomenon and the possibly related clinical reduction of spasticity, spasms and cramps. A tachyphalaxis or desensitization phenomenon, perhaps similar to the clinical autorefractory state, has been noted in animal lower motor neurons with larger amounts of TRH micropipetted into the spinal cord (Nicoll and Phillis, et al., supra). A "trophic-like" action of TRH on neurons may be occurring in responsive patients, analogous to the trophic-like effect of TRH or insulin on tissue-cultured fetal rat lower motor neurons, resulting in chronically enhanced cholineactyltransferase 17- and 10-fold respectively.

In summary, the convenience of subcutaneous TRH and its more prolonged effect demonstrates that symptomatic treatment, e.g., using 50–150 mg once or twice daily every one to three days, of spasticity and lower motor neuron weakness is beneficial in ALS and other disorders involving symptoms consequent to upper and lower motor neuron dysfunction. It should be understood, however, that the exact pattern (amount and frequency) of administration must be tailored to each patient empirically according to clinical responses, in the approximately same manner as insulin therapy in diabetes mellitus.

Moreover, it should be noted that the administration of TRH appears to enhance the function of lower motor neurons which are not directly affected by the diseases specifically treated herein. Accordingly, TRH may be employed to increase the neuronic function where there is no current disease activity. For example, years after the remission of poliomyelitis, the function of the remaining lower motor neurons may be increased and strength consequently enhanced.

In addition, more convenient delivery (such as oral administration) the development of a longer-acting TRH analogue, or analogue of the active derivative, with a higher benefit/side effect ratio; use of an inhibitor to slow catabolism of TRH or its active derivative; the ability to modify the responsiveness of females and males to TRH, its derivatives or its analogues and other variations may provide additional advantages which are within the spirit of the described invention.

I claim:

1. A method for improving a dysfunction of the lower motor neurons or upper motor neurons in a mammal, comprising the repeated administration to the mammal suffering from said dysfunction of a therapeutically-effective amount of TRH.

2. The method foc claim 1 wherein the improvement comprises the alleviation of the chronic symptoms of spasticity, weakness or pain.

3. The method of claim 1 wherein the dysfunction is present in a mammal having a disease selected from the group consisting of amyothrophic lateral sclerosis, juvenile proximal spinal muscular atrophy, infantile spinal muscular atrophy, chronic adult progressive muscular atrophy, chronic hereditary dysneuronal neuropathy, primary lateral sclerosis, adrenomyeloneuropathy and multiple sclerosis.

4. The method of claim 1, 2 or 3 wherein the TRH is administered subcutaneously.

5. A method for the symptomatic treatment of chronic spasticity consequent to upper motor neuron dysfunction in a patient, comprising the repeated administration of an amount of TRH effective to alleviate said spasticity to a patient suffering from said dysfunction.

6. The method of claim 5 wherein the spasticity is present in a patient having amyotrophic lateral sclerosis, lateral sclerosis, adrenomyeloneuropathy or multiple sclerosis.

7. The method of claim 5 or 6 wherein the TRH is administered subcutaneously.

8. A method for the symptomatic treatment of chronic weakness consequent to lower motor neuron dysfunction in a patient, comprising the repeated administration an amount of TRH effective to alleviate said weakness to a patient suffering from said dysfunction.

9. The method of claim 8 wherein the weakness is present in a patient having proximal spinal muscular atrophy, progressive muscular atrophy or dysneuronal neuropathy.

10. The method of claim 8 or 9 wherein the TRH is administered subcutaneously.

11. A method for treating chronic pain in a patient, comprising the repeated administration an amount of TRH effective to alleviate said pain to a patient suffering from said pain.

12. A method for the symptomatic treatment of chronic pain associated with a dysfunction of the lower or upper motor neurons in a patient, comprising the repeated administration of an amount of TRH effective to alleviate said pain to a patient suffering from said dysfunction.

13. The method of claim 12 wherein the pain is present in a patient having a disease selected from the group consisting of amyothrophic lateral sclerosis, juvenile proximal spinal muscular atrophy, infantile spinal muscular atrophy, chronic adult progressive muscular atrophy, chronic hereditary dysneuronal neuropathy, primary lateral sclerosis, adrenomyeloneuropathy, and multiple sclerois.

14. The method of claim 11, 12, or 13 wherein the TRH is administered subcutaneously.

15. A method for the symptomatic treatment of muscle spasms consequent to upper motor neuron dysfunction in a patient, comprising the repeated administrtion of an amount of TRH effective to alleviate said muscle spasms to a patient suffering from said dysfunction.

16. The method of claim 15 wherein the muscle spasms are present in a patient having amyotrophic lateral sclerosis, primary lateral sclerosis, adrenomyeloneuropathy or multiple sclerosis.

17. The method of 15 or 16 wherein TRH is administered subcutaneously.

18. A method for the symtomatic treatment of muscle cramps consequent to lower motor neuron dysfunction in a patient, comprising the repeated administration of an amount of TRH effective to alleviate said muscle cramps to a patient suffering from said dysfunction.

19. The method of claim 18 wherein the muscle cramps are present in a patient having proximal spinal muscular atrophy, progressive muscular atrophy or dysneuronal neuropathy.

20. The method of claim 8 or 9 wherein the TRH is administered subcutaneously.

21. A method for the treatment of the symptoms of the disease of amyotrophic lateral sclerosis in a mammal, comprising the repeated administration to the mammal of an amount of TRH that is thereapeutically effective for said treatment.

22. The method of claim 21 wherein the TRH is administered subcutaneously.

23. A method for the treatment of the symptoms of the disease of juvenile proximal spinal muscular atrophy in a mammal, comprising the repeated administration to the mammal of an amount of TRH that is therapeutically effective for said treatment.

24. The method of claim 23 wherein the TRH is administered subcutaneously.

25. A method for the treatment of the symptoms of the disease of infantile spinal muscular atrophy in a mammal, comprising the repeated administration to the mammal of an amount of TRH that is therapeutically effective for said treatment.

26. The method of claim 25 wherein the TRH is administered subcutaneously.

27. A method for the treatment of the symptoms of the disease of chronic adult progressive muscular atrophy in a mammal, comprising the repeated administration to the mammal of an amount of TRH that is therapeutically effective for said treatment.

28. The method of claim 27 wherein the TRH is administered subcutaneously.

29. A method for the treatment of the symptoms of the disease of dysneuronal neuropathy in a mammal, comprising the repeated administration to the mammal of an amount of TRH that is therapeutically effective for said treatment.

30. The method of claim 29 wherein the TRH is administered subcutaneously.

31. A method for the treatment of the symptoms of the disease of primary lateral sclerosis in a mammal, comprising the repeated administration to the mammal of an amount of TRH that is therapeutically effective for said treatment.

32. The method of claim 31 wherein the TRH is administered subcutaneously.

33. A method for the treatment of the symptoms of the disease of adrenomyeloneuropathy in a mammal, comprising the repeated administration to the mammal of an amount of TRH that is therapeutically effective for said treatment.

34. The method of claim 33 wherein the TRH is administered subcutaneously.

35. A method for the treatment of the symptoms of the disease of multiple sclerosis in a mammal, comprising the repeated administration to the mammal of an amount of TRH that is therapeutically effective for said treatment.

36. The method of claim 35 wherein the TRH is administered subcutaneously.

* * * * *